United States Patent
Ueda et al.

(10) Patent No.: US 10,702,196 B2
(45) Date of Patent: *Jul. 7, 2020

(54) PULSE PHOTOMETER

(71) Applicant: NIHON KOHDEN CORPORATION, Shinjuku-ku, Tokyo (JP)

(72) Inventors: Yoshinori Ueda, Tokyo (JP); Teiji Ukawa, Tokyo (JP); Kazumasa Ito, Tokyo (JP); Hideki Fujisaki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 288 days.

This patent is subject to a terminal disclaimer.

(21) Appl. No.: 15/819,619

(22) Filed: Nov. 21, 2017

(65) Prior Publication Data

US 2018/0092579 A1 Apr. 5, 2018

Related U.S. Application Data

(63) Continuation of application No. 14/662,476, filed on Mar. 19, 2015, now Pat. No. 9,854,999.

(30) Foreign Application Priority Data

Mar. 28, 2014 (JP) ................... 2014-068791

(51) Int. Cl.
*A61B 5/1455* (2006.01)
*A61B 5/024* (2006.01)
(Continued)

(52) U.S. Cl.
CPC ...... *A61B 5/14551* (2013.01); *A61B 5/02416* (2013.01); *A61B 5/742* (2013.01);
(Continued)

(58) Field of Classification Search
CPC .............. A61B 5/1455; A61B 5/14551; A61B 5/02416; A61B 5/742; A61B 5/7455; A61B 5/7405; A61B 5/7221; A61B 5/7214

See application file for complete search history.

(56) References Cited

U.S. PATENT DOCUMENTS 4,623,248 A 11/1986 Sperinde
6,226,540 B1 5/2001 Bernreuter
(Continued)

FOREIGN PATENT DOCUMENTS

JP 4196209 B2 12/2008

OTHER PUBLICATIONS

Extended European Search Report dated Aug. 20, 2015, by the European Patent Office in counterpart European Application No. 15160123.4.

*Primary Examiner* — Eric F Winakur
*Assistant Examiner* — Chu Chuan Liu
(74) *Attorney, Agent, or Firm* — Sughrue Mion, PLLC

(57) ABSTRACT

A pulse photometer includes a light emitter, a light detector, a first signal separator that separates a first signal component and a first noise component, a second signal separator that separates a second signal component and a second noise component, a first determining section, a second determining section, and a concentration calculating section that calculates a concentration of a light absorption material in blood of the subject based on a fundamental frequency of the first signal component or a fundamental frequency of the second signal component.

14 Claims, 4 Drawing Sheets

(51) Int. Cl.
 *A61B 5/00* (2006.01)
 *G01N 21/31* (2006.01)
 *G01N 33/49* (2006.01)
(52) U.S. Cl.
 CPC .......... *A61B 5/7405* (2013.01); *A61B 5/7455* (2013.01); *G01N 21/31* (2013.01); *G01N 33/4925* (2013.01); *A61B 5/7214* (2013.01); *A61B 5/7221* (2013.01); *G01N 2201/061* (2013.01); *G01N 2201/12* (2013.01)

(56) References Cited

U.S. PATENT DOCUMENTS

| | | |
|---|---|---|
| 6,334,065 B1 | 12/2001 | Al-Ali et al. |
| 7,257,433 B2 | 8/2007 | Takamura et al. |
| 2001/0005773 A1 | 6/2001 | Larsen et al. |
| 2002/0042558 A1 | 4/2002 | Mendelson |
| 2002/0082489 A1 | 6/2002 | Casciani et al. |
| 2004/0267140 A1 | 12/2004 | Ito et al. |
| 2012/0253153 A1 | 10/2012 | Trumble |

PULSE PHOTOMETER

CROSS REFERENCE TO RELATED APPLICATION

This application is a Continuation Application of U.S. patent application Ser. No. 14/662,476, filed Mar. 19, 2015, which is based on Japanese Patent Applications No. 2014-068791 filed on Mar. 28, 2014, the contents of which are incorporated herein by reference in their entireties.

BACKGROUND

The presently disclosed subject matter relates to a pulse photometer.

A pulse photometer is an apparatus which irradiates the living tissue of the subject with light beams at a plurality of wavelengths having different light absorption properties of a light absorption material in blood, and which measures the intensities of the light beams at the wavelengths transmitted through or reflected from the living tissue, thereby calculating the concentration of the light absorption material in blood. The intensities of the light beams are acquired in the form of a pulse wave signal corresponding to the absorbance which is changed in accordance with the pulsation of the blood. Japanese Patent No. 4,196,209 discloses a technique in which, in order to reduce noises from a pulse wave signal, the affine transformation is performed by using a known absorbance ratio (a ratio of absorbances at wavelengths).

In the technique disclosed in Japanese Patent No. 4,196,209, the result of a past measurement in which it was determined that there is no noise contamination is used as the known absorbance ratio. In the case where the absorbance ratio obtained from a pulse wave signal, and that obtained from a noise signal have similar values, however, there is a possibility that the absorbance ratio in the noise signal is employed as the known absorbance ratio. When such erroneous employment occurs, the subsequent noise removal process relies on a value based on the noise signal, and therefore the calculation of the concentration of the light absorption material in blood may lack accuracy.

Therefore, it is an object of the presently disclosed subject matter to improve the accuracy of the calculation of the concentration of a light absorption material in blood.

SUMMARY

In order to attain the object, an aspect of the presently disclosed subject matter is a pulse photometer including:

an emitter which emits at least three kinds of light beams at different wavelengths;

a detector which outputs at least three kinds of intensity signals in accordance with intensities of the at least three kinds of light beams that are transmitted through or reflected from a living tissue of a subject;

a first signal separator which separates a first signal component and a first noise component based on intensity signals of two kinds of light beams in a first combination selected from the at least three kinds of light beams;

a second signal separator which separates a second signal component and a second noise component based on intensity signals of two kinds of light beams in a second combination selected from the at least three kinds of light beams;

a first determining section which determines whether a first difference between a first signal absorbance ratio of the first signal component and a first noise absorbance ratio of the first noise component is smaller than a first predetermined value or not;

a second determining section which, if it is determined that the first difference is smaller than the first predetermined value, determines whether a second difference between a second signal absorbance ratio of the second signal component and a second noise absorbance ratio of the second noise component is smaller than a second predetermined value or not; and a concentration calculating section which, if it is determined that the first difference is equal to or larger than the first predetermined value, calculates a concentration of a light absorption material in blood of the subject based on a fundamental frequency of the first signal component, and, if it is determined that the second difference is equal to or larger than the second predetermined value, calculates the concentration of the light absorption material in blood based on a fundamental frequency of the second signal component.

According to the configuration, at least two combinations of two kinds of light beams are produced by using at least three kinds of light beams at different wavelengths. In the case where the difference between the absorbance ratio of the signal component obtained from the first combination and that of the noise component is small (in the case where there is a possibility that the noise component is mistaken for the signal component), the absorbance ratio of the signal component obtained from the second combination and that of the noise component are compared to each other. Only when, in any one of the combinations, it is determined that the signal component is distinguishable from the noise component, the concentration of a light absorption material in blood is calculated based on the absorbance ratio of this signal component. Therefore, the accuracy of the calculation of the concentration of a light absorption material in blood can be improved.

Each of the first combination and the second combination may include an infrared red light beam and a red light beam as the two kinds of light beams.

According to the configuration, the accuracy of the calculation can be improved particularly in a pulse oximeter which calculates the arterial oxygen saturation as the concentration of a light absorption material in blood.

The wavelengths of the at least three kinds of light beams may be, for example, 660 nm, 700 nm, and 880 nm.

In the case where four kinds of light beams are used, the wavelengths of the light beams may be, for example, 660 nm, 700 nm, 730 nm, and 880 nm, or 660 nm, 700 nm, 880 nm, and 940 nm.

The pulse photometer may further include a notifying section which, if it is determined that the second difference is smaller than the second predetermined value, notifies of an error state.

The determination by the second determining section is performed in the case where the first determining section determines that there is a possibility that the signal and noise components obtained from the two kinds of light beams in the first combination selected from the at least three kinds of light beams in different wavelengths are not distinguishable from each other. When, with respect to the two kinds of light beams at the second combination selected from the at least three kinds of light beams, the absorbance ratio of the signal component and that of the noise component are compared to each other, a result which is different from that the determination by the first determining section is usually obtained. In the case where also the second determining section determines that there is a possibility that the signal and noise components are not distinguishable from each other, the probability that some kind of trouble occurs in the pulse photometer or the measurement environment is high. According to the configuration, the probability of an error state is notified at an early stage, and hence it is possible to prevent the measurement from being continued while the trouble remains unsolved. Therefore, the accuracy of the calculation of the concentration of a light absorption material in blood can be improved.

DETAILED DESCRIPTION OF EMBODIMENTS

Figure 1:
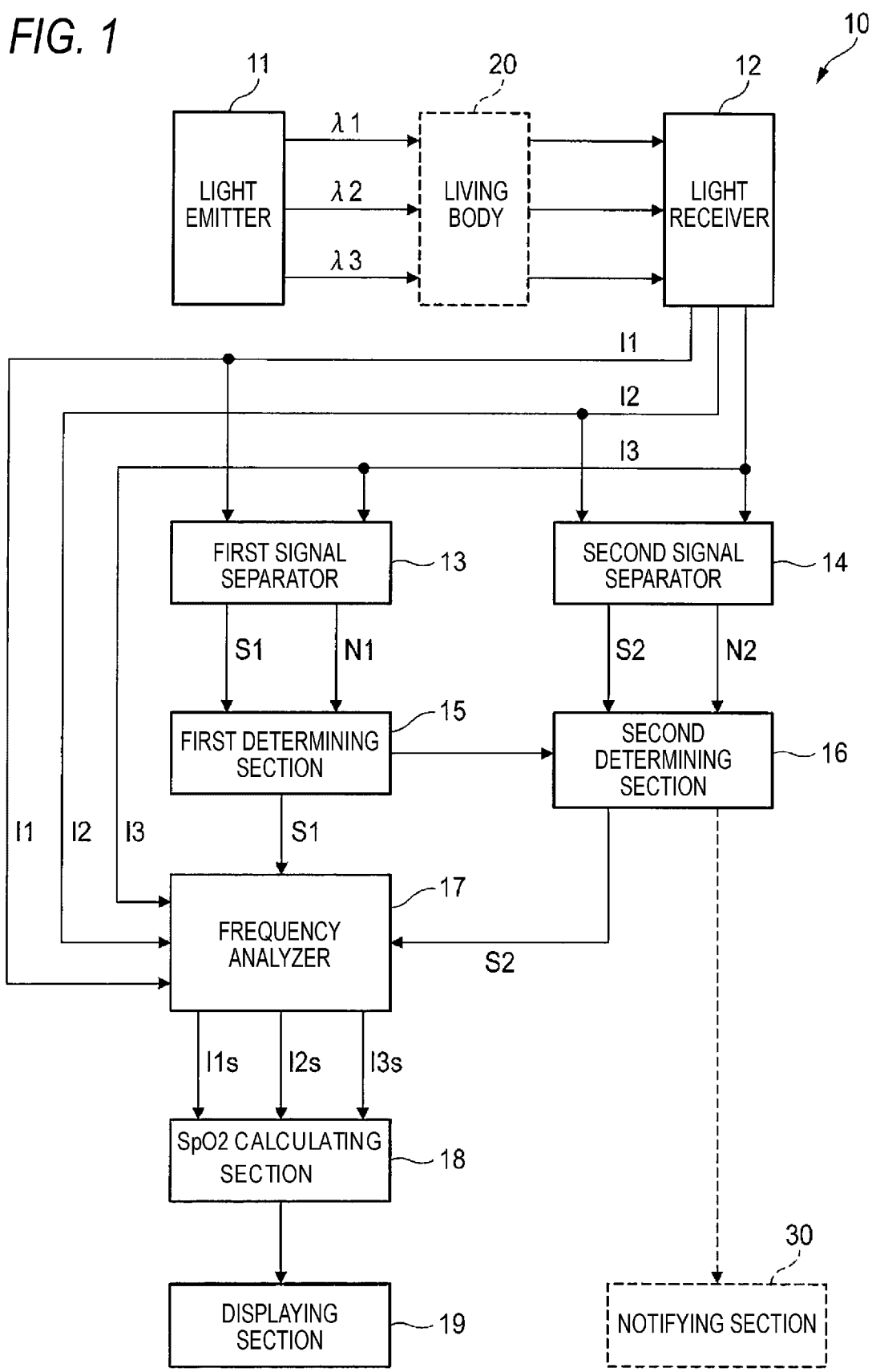
FIG. 1 is a block diagram illustrating the functional configuration of a pulse oximeter of an embodiment of the presently disclosed subject matter.

An embodiment of the presently disclosed subject matter will be described in detail with reference to the accompanying drawings. FIG. 1 is a block diagram illustrating the functional configuration of a pulse oximeter 10 (an example of the pulse photometer) of an embodiment of the presently disclosed subject matter. The pulse oximeter 10 is an apparatus which measures the arterial oxygen concentration (hereinafter, referred to as SpO2) of the subject. The SpO2 indicates a rate (an example of the concentration of the light absorption material in blood) of oxyhemoglobin (an example of the light absorption material in blood) to the amount of hemoglobin capable of carrying oxygen.

The pulse oximeter 10 can include a light emitter 11. The light emitter 11 can emit a first light beam having a wavelength $\lambda 1$, a second light beam having a wavelength $\lambda 2$, and a third light beam having a wavelength $\lambda 3$. The wavelengths $\lambda 1$, $\lambda 2$, and $\lambda 3$ are different from each other. In the embodiment, the wavelength $\lambda 1$ is 660 nm, the wavelength $\lambda 2$ is 700 nm, and the wavelength $\lambda 3$ is 880 nm. Namely, the first and second light beams are red light beams, and the third light beam is an infrared red light beam. For example, the light emitter 11 is a semiconductor light emitting device which can emit light beams at these wavelengths. Examples of the semiconductor light emitting device are a light emitting diode (LED), a laser diode, and an organic electroluminescence (EL) device.

The pulse oximeter 10 can include a light detector 12. The light detector 12 can receive the first, second, and third light beams which have been passed through or reflected from the living body 20 of the subject. The light detector 12 outputs a first intensity signal I1 corresponding to the intensity of the received first light beam, a second intensity signal I2 corresponding to the intensity of the received second light beam, and a third intensity signal I3 corresponding to the intensity of the received third light beam. For example, the light detector 12 is an optical sensor having a sensitivity to the wavelengths of the light beams emitted from the light emitter 11. An example of the optical sensor is a photodiode, a photodiode and a photoresistor.

The pulse oximeter 10 can include a first signal separator 13. The first signal separator 13 separates a first signal component S1 and a first noise component N1 based on the first and third intensity signals I1, I3 (an example of the intensity signals of the two light beams in the first combination).

Figure 2A:
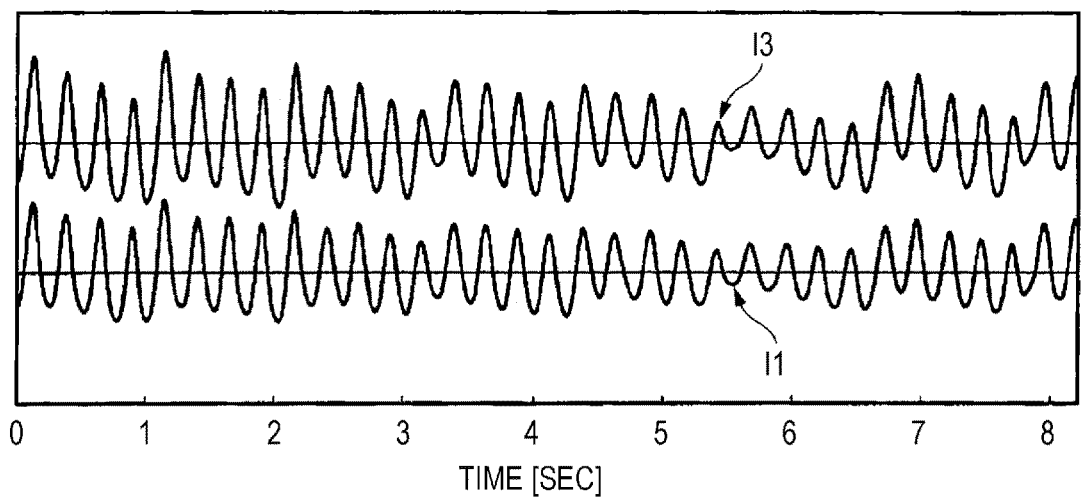
FIGS. 2A to 2D illustrate a signal separation process which is executed by the pulse oximeter.
Figure 2B:
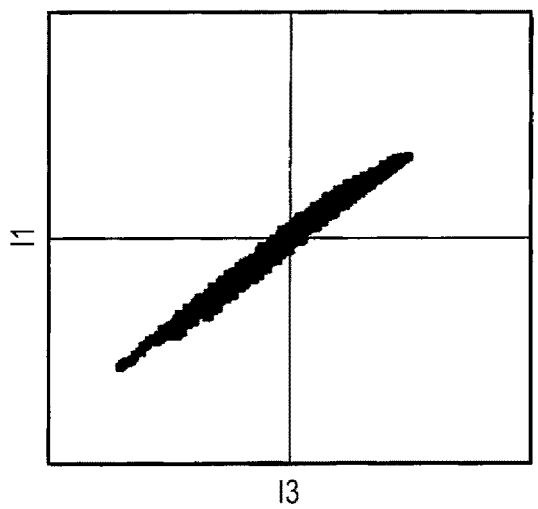
Figure 2C:
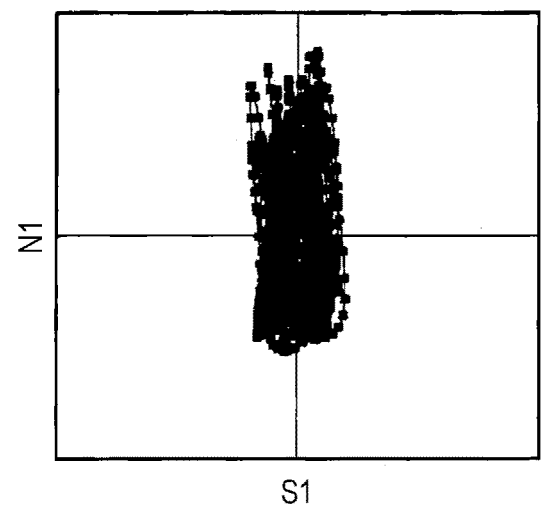
Figure 2D:
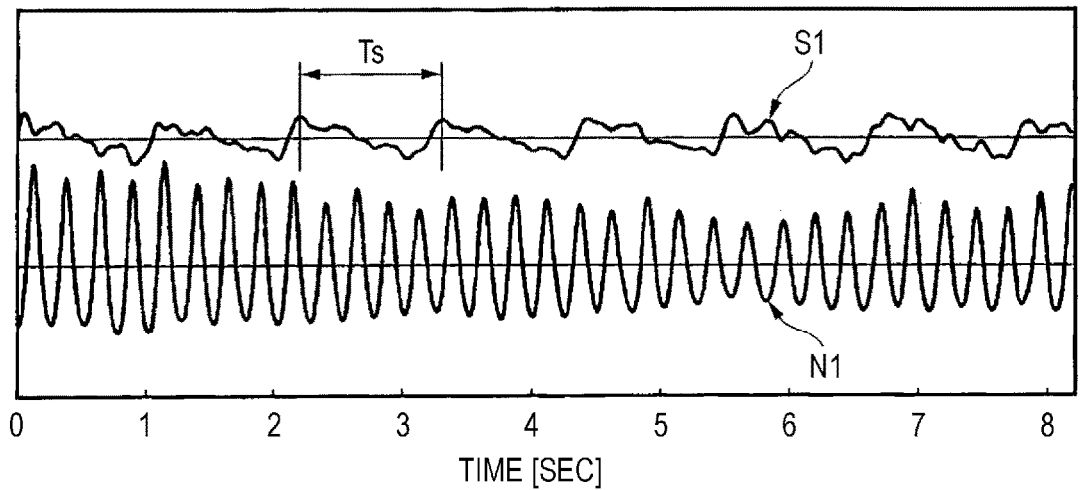
Figure 3:
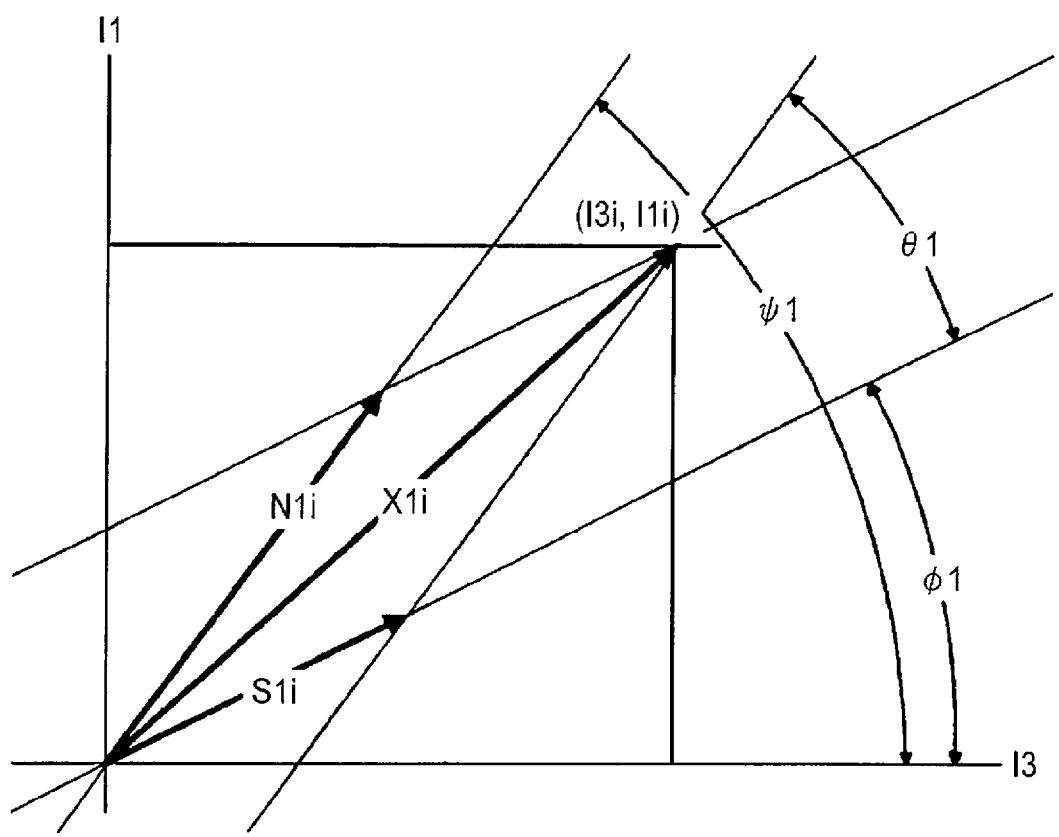
FIG. 3 illustrates the signal separation process which is executed by the pulse oximeter.

Referring to FIGS. 2A to 3, the operation of the first signal separator 13 will be described in detail. FIG. 2A illustrates temporal changes of the first intensity signal I1 and third intensity signal I3 which are acquired from the light detector 12, and which are output to the first signal separator 13. The first intensity signal I1 and the third intensity signal I3 are referred to as a first observed signal pair.

FIG. 3 illustrates a coordinate plane in which the ordinate represents the amplitude of the first intensity signal I1, and the abscissa represents the amplitude of the third intensity signal I3. The first observed signal pair at a certain timing $t=ti$ is indicated by a vector X1$i$ in which the end coordinates are (I3$i$, I1$i$). The vector X1$i$ is decomposed into a vector S1$i$ indicating the first signal component, and a vector N1$i$ indicating the first noise component. In other words, the vector X1$i$ is a resultant vector of the vector S1$i$ and the vector N1$i$.

The slope angle of the vector S1$i$ to the abscissa is represented by $\phi 1$, and that of the vector N1$i$ to the abscissa is represented by $\varphi 1$. The relationships of I1$i$, I3$i$, S1$i$, and Ni1 are indicated by the following expression.

[Exp. 1]

$$\begin{pmatrix} I3i \\ I1i \end{pmatrix} = \begin{pmatrix} \cos\phi 1 & \cos\varphi 1 \\ \sin\phi 1 & \sin\varphi 1 \end{pmatrix} \begin{pmatrix} S1i \\ N1i \end{pmatrix} \quad (1)$$

Here, the following expression is assumed.

[Exp. 2]

$$W = \begin{pmatrix} \cos\phi 1 & \cos\varphi 1 \\ \sin\phi 1 & \sin\varphi 1 \end{pmatrix} \quad (2)$$

When an inverse matrix A of W is applied to the first observed signal pair as in the following expression, the first signal component S1 and the first noise component N1 are separated.

[Exp. 3]

$$\begin{pmatrix} S1i \\ N1i \end{pmatrix} = A \begin{pmatrix} I3i \\ I1i \end{pmatrix} \quad (3)$$

This operation represents that the first signal component S1 is transferred to the abscissa, and the first noise component N1 is transferred to the ordinate. The inverse matrix A is obtained as the following expression.

[Exp. 4]

$$A = \begin{pmatrix} \cos\phi 1 & \cos\varphi 1 \\ \sin\phi 1 & \sin\varphi 1 \end{pmatrix}^{-1} \quad (4)$$

$$= \frac{1}{\sin(\varphi 1 - \phi 1)} \begin{pmatrix} \sin\varphi 1 & -\cos\varphi 1 \\ -\sin\phi 1 & \cos\phi 1 \end{pmatrix}$$

$$= \begin{pmatrix} 1 & -\frac{1}{\tan\theta 1} \\ 0 & \frac{1}{\sin\theta 1} \end{pmatrix} \begin{pmatrix} \cos\phi 1 & \sin\phi 1 \\ -\sin\phi 1 & \cos\phi 1 \end{pmatrix}$$

Therefore, the following expression is obtained from Expressions (3) and (4).

[Exp. 5]

$$\begin{pmatrix} S1i \\ N1i \end{pmatrix} = \begin{pmatrix} 1 & -\frac{1}{\tan\theta 1} \\ 0 & \frac{1}{\sin\theta 1} \end{pmatrix} \begin{pmatrix} \cos\phi 1 & \sin\phi 1 \\ -\sin\phi 1 & \cos\phi 1 \end{pmatrix} \begin{pmatrix} I3i \\ I1i \end{pmatrix} \quad (5)$$

The coordinate transformation indicated by Expression (5) corresponds to the transformation from a first coordinate system which is shown in FIG. 2B, and in which the two kinds of intensity signals I1, I3 are selected as the coordinate axes, to a second coordinate system which is shown in FIG. 2C, and in which the first signal component S1 and the first noise component N1 are selected as the coordinate axes.

The coordinate transformation begins from an operation of making the vector S1i coincident with the abscissa of the transformed coordinate system. Specifically, an operation of rotating the vector S1i in FIG. 3 by the angle ϕ1 in a clockwise direction is performed. The following relationship is held between ϕ1 and an absorbance ratio Φ1, and therefore ϕ1 is obtained from the following expression by using the known Φ1.

$$\Phi 1 = \tan \phi 1 \quad (6).$$

When the time period to be considered is sufficiently short as compared with the pulsation interval time, the just previous value (for example, the value before 10 milliseconds), or an absorbance ratio in which it was determined that there is no noise contamination may be used as the value of Φ.

In Expression (5), θ1 is a coefficient corresponding to an operation of making the vector N1i coincident with the ordinate of the transformed coordinate system. The value of φ1 corresponding to the absorbance ratio of the first noise component N1 is unknown. In order to determine θ1 functioning as a transformation coefficient as a single value, therefore, θ1 is changed in the range from −ϕ1 to (π/2)−ϕ1, and a value at which the norm in the direction of the abscissa in the transformed coordinate system is minimum is employed as θ1.

FIG. 2D illustrates waveforms of the first signal component S1 and first noise component N1 which are separated by the process performed by the first signal separator 13. In the first signal component S1, a periodic change of the amplitude due to the pulsation of the blood can be seen. The inverse of the period Ts of the change is defined as the fundamental frequency of the first signal component S1.

As shown in FIG. 1, the pulse oximeter 10 can include a second signal separator 14. The second signal separator 14 separates a second signal component S2 and a second noise component N2 based on the second and third intensity signals I2, I3 (an example of the intensity signals of the two kinds of light beams in the second combination).

The second signal separator 14 applies a similar process as that in the first signal separator 13 to a second observed signal pair configured by the second and third intensity signals I2, I3. In FIGS. 2A to 3 and Expressions (1), (3), and (5), namely, I1 is replaced with I2, S1i and N1i are replaced with S2i and N2i. Furthermore, ϕ1, φ1, and θ1 are replaced with ϕ2, φ2, and θ2.

As shown in FIG. 1, the pulse oximeter 10 can include a first determining section 15, a second determining section 16, a frequency analyzer 17, and an SpO2 calculating section 18. The operations of these sections will be described with reference to FIG. 4.

Figure 4:
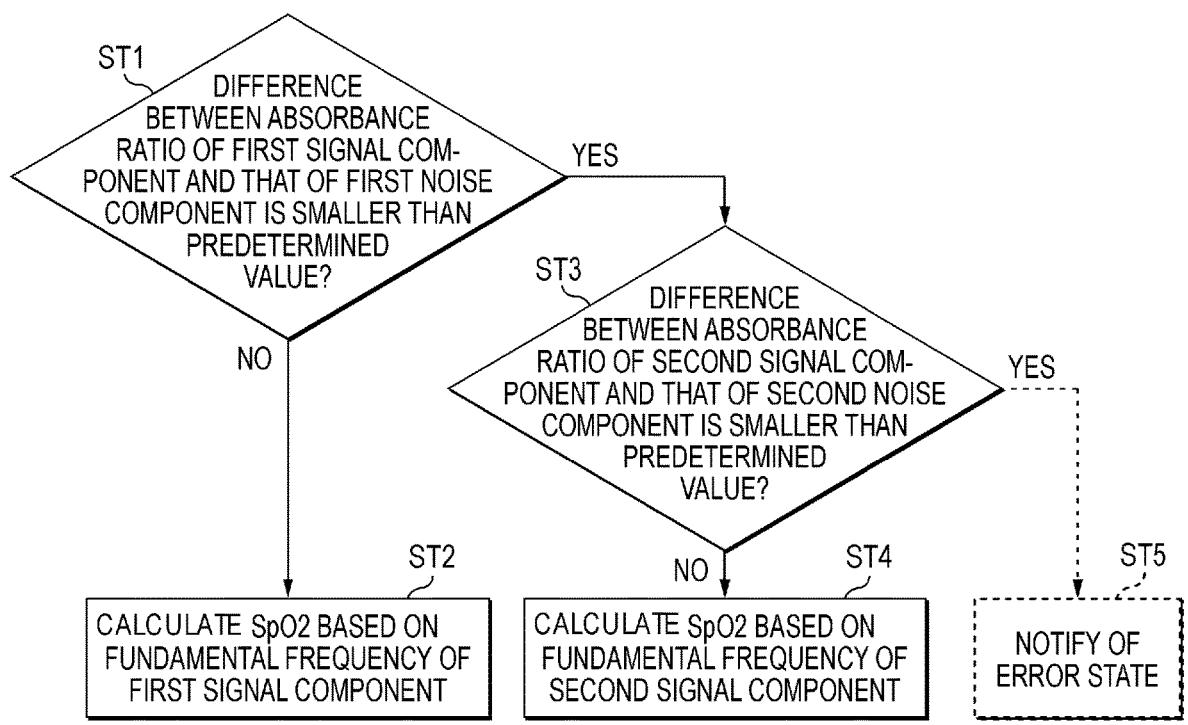
FIG. 4 is a flowchart illustrating a part of a process which is executed by the pulse oximeter.

The first determining section 15 determines whether a difference (first difference) between the absorbance ratio of the first signal component S1 and that of the first noise component N1 is smaller than a predetermined threshold (first predetermined value) or not (step ST1 of FIG. 4). As described above, ϕ1 in FIG. 3 corresponds to the absorbance ratio of the first signal component S1, and φ1 corresponds to the absorbance ratio of the first noise component N1. Therefore, the first difference corresponds to θ1.

If the first determining section 15 determines that the first difference θ1 is equal to or larger than the first predetermined value (No in step ST1 of FIG. 4), in FIG. 3, the vector S1i and the vector N1i are sufficiently separated from each other. In this case, the first signal component S1 and the first noise component N1 are clearly distinguishable from each other. Therefore, the frequency analyzer 17 can easily calculate the fundamental frequency of the above-described first signal component S1.

The frequency analyzer 17 filters the first intensity signal I1, the second intensity signal I2, and the third intensity signal I3 with the calculated fundamental frequency. According to the configuration, a change of the received light intensity due to the pulsation of the blood can be surely extracted. The frequency analyzer 17 outputs a first output signal I1s, a second output signal I2s, and a third output signal I3s. The first output signal I1s corresponds to the first intensity signal I1 which has undergone the filtering. Similarly, the second output signal I2s and the third output signal I3s correspond to the second intensity signal I2 and third intensity signal I3 which have undergone the filtering, respectively.

The SpO2 calculating section 18 (an example of the concentration calculating section) calculates the SpO2 based on the first output signal I1s, the second output signal I2s, and the third output signal I3s (step ST2 of FIG. 4). Namely, it can be said that the SpO2 calculating section 18 calculates the SpO2 based on the fundamental frequency of the first signal component S1.

The SpO2 calculating section 18 acquires a first light attenuation change ΔA1 due to the blood pulsation based on the first output signal I1s, a second light attenuation change ΔA2 due to the blood pulsation based on the second output signal I2s, and a third light attenuation change ΔA3 due to the blood pulsation based on the third output signal I3s. The light attenuation changes ΔA1, ΔA2, and ΔA3 are expressed by the following expressions:

$$\Delta A1 = \ln[I1s/(I1s - \Delta I1s)] \approx \Delta I1s/I1s \quad (7)$$

$$\Delta A2 = \ln[I2s/(I2s - \Delta I2s)] \approx \Delta I2s/I2s \quad (8)$$

$$\Delta A3 = \ln[I3s/(I3s - \Delta I3s)] \approx \Delta I3s/I3s \quad (9)$$

where ΔI1s, ΔI2s, and ΔI3s indicate changes of output signals related to the first, second, and third light beams due to the blood pulsation, respectively.

The SpO2 calculating section 18 acquires blood-derived light attenuation changes based on the first and second light attenuation changes ΔA1, ΔA2, and the second and third light attenuation changes ΔA2, ΔA3. Specifically, the SpO2 calculating section acquires a blood-derived light attenuation change Ab21 based on the difference between the light attenuation changes ΔA1, ΔA2, and a blood-derived light attenuation change Ab23 based on the difference between the light attenuation changes ΔA2, ΔA3. The light attenuation changes ΔA1, ΔA2, and ΔA3 are expressed by the following expressions:

$$\Delta A1 = \Delta Ab1 + \Delta At1 = E1Hb\Delta Db + Z1\Delta Dt \quad (10)$$

$$\Delta A2 = \Delta Ab2 + \Delta At2 = E2Hb\Delta Db + Z2\Delta Dt \quad (11)$$

$$\Delta A3 = \Delta Ab3 + \Delta At3 = E3Hb\Delta Db + Z3\Delta Dt \quad (12)$$

where E is the extinction coefficient of blood (dl g$^{-1}$ cm$^{-1}$), Hb is the hemoglobin concentration of blood (g dl$^{-1}$), Z is the light attenuation rate (cm$^{-1}$) of the tissue except blood, and ΔD is the thickness change (cm) due to the blood pulsation. The suffix "b" means blood, the suffix "t" means the tissue except blood, the suffix "1" means the first light beam, the suffix "2" means the second light beam, and the suffix "3" means the third light beam.

The wavelength dependency of the tissue except blood can be neglected. Therefore, it can be deemed that Z1=Z2=Z3. When Expression (10) is subtracted from Expression (11), and Expression (12) is subtracted from Expression (11), the following expressions are obtained:

$$Ab21 = \Delta A2 - \Delta A1 = (E2-E1)Hb\Delta Db \qquad (13)$$

$$Ab23 = \Delta A2 - \Delta A3 = (E2-E3)Hb\Delta Db \qquad (14).$$

The right side contains only information of blood. When the difference of the light attenuation change ΔA1 and the light attenuation ΔA2, and that of the light attenuation change ΔA2 and the light attenuation change ΔA3 are obtained, therefore, it is possible to acquire the blood-derived light attenuation changes Ab21 and Ab23.

Next, Expression (14) is divided by Expression (13), the terms of Hb and ΔDb are deleted, and the following expression is obtained:

$$Ab23/Ab21 = (\Delta A2 - \Delta A3)/(\Delta A2 - \Delta A1) \qquad (15)$$

$$= (E2-E3)/(E2-E1).$$

In Expression (15), (E2−E1) and (E2−E3) are functions of the SpO2. Therefore, also the ratio of (E2−E3) to (E2−E1) is a function of the SpO2. When the SpO2 which is expressed in a percentage notification is expressed as S which is expressed in a decimal notification, the extinction coefficients of blood E1, E2, and E3 are expressed by the following expressions:

$$E1 = Eo1S + Er1(1-S) \qquad (16)$$

$$E2 = Eo2S + Er2(1-S) \qquad (17)$$

$$E3 = Eo3S + Er3(1-S) \qquad (18)$$

where Eo is the extinction coefficient of oxyhemoglobin, and Er is the extinction coefficient of deoxyhemoglobin. In the same manner as described above, the suffix "1" means the first light beam, the suffix "2" means the second light beam, and the suffix "3" means the third light beam.

From the above, it is seen that, when the blood-derived light attenuation change Ab21 and Ab23 are measured by using light beams having at least three kinds of wavelengths, the SpO2 can be quantitatively calculated through Expressions (15) to (18). The SpO2 calculating section 18 calculates the SpO2 based on the principle.

When the first difference θ1 is small, by contrast, the vector S1i and the vector N1i are close to each other in FIG. 3, the first noise component N1 may be mistaken for the first signal component S1. In the embodiment, when the first determining section 15 determines that the first difference θ1 is smaller than the first predetermined value (Yes in step ST1 of FIG. 4), therefore, the second determining section 16 operates.

The second determining section 16 determines whether a difference (second difference) between the absorbance ratio of the second signal component S2 and that of the second noise component N2 is smaller than a predetermined threshold (second predetermined value) or not (step ST3 of FIG. 4). The absorbance ratio of the second signal component S2 corresponds to ϕ2 which is a replacement of ϕ1 in FIG. 3. The absorbance ratio of the second noise component N2 corresponds to φ2 which is a replacement of φ1 in FIG. 3. The second difference corresponds to φ2 which is a replacement of θ1 in FIG. 3.

If the second determining section 16 determines that the second difference θ2 is equal to or larger than the second predetermined value (No in step ST3 of FIG. 4), in FIG. 3, the vector S2i and the vector N2i are sufficiently separated from each other. In this case, the second signal component S2 and the second noise component N2 are clearly distinguishable from each other. Therefore, the frequency analyzer 17 can easily calculate the fundamental frequency of the second signal component S2.

The frequency analyzer 17 filters the first intensity signal I1, the second intensity signal I2, and the third intensity signal I3 with the fundamental frequency which is calculated based on the second signal component S2, and outputs the first output signal I1s, the second output signal I2s, and the third output signal I3s. The SpO2 calculating section 18 calculates the SpO2 based on the first output signal I1s, the second output signal I2s, and the third output signal I3s (step ST4 of FIG. 4). Namely, it can be said that the SpO2 calculating section 18 calculates the SpO2 based on the fundamental frequency of the second signal component S2. The process of calculating the SpO2 is similar to that in the case where the SpO2 is calculated based on the first signal component S1.

As shown in FIG. 1, the pulse oximeter 10 can include a displaying section 19. The displaying section 19 displays the SpO2 which is calculated by the SpO2 calculating section 18.

As described above, according to the pulse oximeter 10 of the embodiment, the two combinations of two kinds of light beams are produced by using the three kinds of light beams at different wavelengths. In the case where the difference between the absorbance ratio of the signal component obtained from one of the combinations, and that of the noise component is small (in the case where there is a possibility that the noise component is mistaken for the signal component), the absorbance ratio of the signal component obtained from the other combination and that of the noise component are compared to each other. Only when, in any one of the combinations, it is determined that the signal component is distinguishable from the noise component, the SpO2 is calculated based on the fundamental frequency of this signal component. Therefore, the accuracy of the calculation of the SpO2 can be improved.

In the embodiment, the first one of the two combinations can include the first light beam (wavelength λ1=660 nm) and the third light beam (wavelength λ3=880 nm), and the second one of the two combinations can include the second light beam (wavelength λ2=700 nm) and the third light beam (wavelength λ3=880 nm). In other words, each of the first and second combinations can include a red light beam and an infrared light beam as the combination of two kinds of light beams.

Since a red light beam and an infrared light beam are a combination in which an absorbance ratio of blood changes due to the arterial oxygen saturation, the accuracy of the calculation of, particularly, the SpO2 can be improved.

As indicated by the broken lines in FIG. 1, the pulse oximeter 10 may further include a notifying section 30. The notifying section 30 notifies of an error state in the case where the second determining section 16 determines that the difference (second difference) between the absorbance ratio of the second signal component S2 and that of the second noise component N2 is smaller than the predetermined threshold (second predetermined value). The error state is notified by means of at least one of the optical notification, the audible notification, and the vibratory notification. This process corresponds to step ST5 which, if Yes in step ST3, is executed as indicated by the broken lines in FIG. 4.

The determination by the second determining section 16 is performed in the case where the first determining section 15 determines that the signal and noise components obtained from the two kinds of light beams in the first combination selected from three kinds of light beams in different wavelengths are not distinguishable from each other. When, with respect to the two kinds of light beams in the second combination selected from the three kinds of light beams, the absorbance ratio of the signal component and that of the noise component are compared to each other, a result which is different from that of the determination by the first determining section 15 is usually obtained. In the case where also the second determining section 16 determines that there is a possibility that the signal and noise components are not distinguishable from each other, the probability that some kind of trouble occurs in the pulse oximeter 10 or the measurement environment is high. According to the configuration, the probability of an error state is notified at an early stage, and hence it is possible to prevent the measurement from being continued while the trouble remains unsolved. Therefore, the accuracy of the calculation of the SpO2 can be improved.

The embodiment described above has been made in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

In the embodiment described above, a pulse oximeter for calculating the SpO2 has been exemplified. However, the presently disclosed subject matter can be applied also to other kinds of pulse photometers which measure the concentration of another light absorption material in blood. Examples of another light absorption material in blood are carbon monoxide hemoglobin, Met-hemoglobin, and a dye injected into blood. In this case, the wavelengths of the three kinds of light beams emitted from the light emitter 11 are selected so that two combinations of two kinds of light beams in which their absorbance ratio of blood changes due to the concentration of the target light absorption material in blood.

The light emitter 11 may emit four or more kinds of light beams at different wavelengths. For example, four wavelengths $\lambda 1$, $\lambda 2$, $\lambda 3$, and $\lambda 4$ are selected as follows:

$\lambda 1=660$ nm, $\lambda 2=700$ nm, $\lambda 3=730$ nm, $\lambda 4=880$ nm; or
$\lambda 1=660$ nm, $\lambda 2=700$ nm, $\lambda 3=880$ nm, $\lambda 4=940$ nm.

When four kinds of light beams are used, it is possible to produce three or more combinations of two kinds of light beams. In this configuration, a third signal component and a third noise component may be separated from observed signals obtained from two kinds of light beams in a third combination. In the case where the second determining section 16 determines that the difference between the absorbance ratio of the second signal component S2 and that of the second noise component N2 is smaller than the predetermined threshold (Yes in step ST3 of FIG. 4), it may be determined whether the difference between the absorbance ratio of the third signal component and that of the third noise component is smaller than a predetermined threshold or not. If the difference is equal to or larger than the threshold, the SpO2 calculating section 18 calculates the SpO2 of the subject based on the fundamental frequency of third signal component. According to the configuration, the accuracy of the calculation of the SpO2 can be further improved.

What is claimed is:

1. A pulse photometer comprising:
   a memory storing instructions;
   a processor configured to execute the instructions;
   an emitter that emits first light beam of a first wavelength, a second light beam of a second wavelength, a third light beam of a third wavelength, and a fourth light beam of a fourth wavelength; and
   a detector that outputs a first intensity signal in accordance with a first intensity of the first light beam that transmitted through or reflected from a living tissue of a subject, a second intensity signal in accordance with a second intensity of the second light beam that is transmitted through or reflected from the living tissue of the subject, a third intensity signal in accordance with a third intensity of the third light beam that is transmitted through or reflected from the living tissue of the subject, and a fourth intensity signal in accordance with a fourth intensity of the fourth light beam that is transmitted through or reflected from the living tissue of the subject,
   wherein the processor executing the instructions stored in the memory is configured to implement functions of:
     a first signal separator that separates a first signal component of a first observed signal pair made of two of the first to fourth intensity signals from a first noise component of the first observed signal pair;
     a second signal separator that separates a second signal component of a second observed signal pair made of two of the first to fourth intensity signals excluding a combination of the first to fourth intensity signals in the first observed signal pair from a second noise component of the second observed signal pair;
     a third signal separator that that separates a third signal component of a third observed signal pair made of two of the first to fourth intensity signals excluding combinations of the first to fourth intensity signals in the first and second observed signal pairs from a third noise component of the third observed signal pair;
     a first determining section that determines whether a first difference between a first signal absorbance ratio of the first signal component and a first noise absorbance ratio of the first noise component is equal to or larger than a first predetermined value;
     a second determining section that determines whether a second difference between a second signal absorbance ratio of the second signal component and a second noise absorbance ratio of the second noise component is equal to or larger than a second predetermined value;
     a third determining section that, when it is determined that the first difference is smaller than the first predetermined value and the second difference smaller than the second predetermined value, determines whether a third difference between a third signal absorbance ratio of the third signal component and a third noise absorbance ratio of the third noise component is equal to or larger than a third predetermined value; and a concentration calculating section that,
  calculates a concentration of a light absorption material in blood of the subject based on a fundamental frequency of the first signal component,
  calculates the concentration of the light absorption material in blood based on a fundamental frequency of the second signal component, or
  calculates the concentration of the light absorption material in blood based on a fundamental frequency of the third signal component in response to the first determining section determining that the first difference is smaller than the first predetermined value and the second determining section determining that the second difference is smaller than the second predetermined value.

2. The pulse photometer according to claim 1, wherein the third light beam is an infrared red light beam, and
  wherein the first light beam and the second light beam are red light beams of different wavelengths.

3. The pulse photometer according to claim 1, further comprising:
  a display that outputs an error state in response to the first determining section determining that the first difference is smaller than the first predetermined value, the second determining section determining that the second difference is smaller than the second predetermined value, and the third determining section determining that the third difference is smaller than the third predetermined value.

4. The pulse photometer according to claim 1, wherein the first wavelength, the second wavelength, and the third wavelength are selected from 660 nm, 700 nm, 730 nm, and 880 nm.

5. The pulse photometer according to claim 1, wherein the first wavelength, the second wavelength, and the third wavelength are selected from are 660 nm, 700 nm, 880 nm, and 940 nm.

6. A pulse photometer comprising:
  a memory storing instructions;
  a processor configured to execute the instructions;
  an emitter that emits first light beam of a first wavelength, a second light beam of a second wavelength, a third light beam of a third wavelength, and a fourth light beam of a fourth wavelength; and
  a detector that outputs a first intensity signal in accordance with a first intensity of the first light beam that transmitted through or reflected from a living tissue of a subject, a second intensity signal in accordance with a second intensity of the second light beam that is transmitted through or reflected from the living tissue of the subject, a third intensity signal in accordance with a third intensity of the third light beam that is transmitted through or reflected from the living tissue of the subject, and a fourth intensity signal in accordance with a fourth intensity of the fourth light beam that is transmitted through or reflected from the living tissue of the subject,
  wherein the processor executing the instructions stored in the memory is configured to implement functions of:
  a first signal separator that separates a first signal component of a first observed signal pair made of two of the first to fourth intensity signals from a first noise component of the first observed signal pair;
  a second signal separator that separates a second signal component of a second observed signal pair made of two of the first to fourth intensity signals excluding a combination of the first to fourth intensity signals in the first observed signal pair from a second noise component of the second observed signal pair;
  a third signal separator that that separates a third signal component of a third observed signal pair made of two of the first to fourth intensity signals excluding combinations of the first to fourth intensity signals in the first and second observed signal pairs from a third noise component of the third observed signal pair;
  a first determining section that determines whether a first difference between a first signal absorbance ratio of the first signal component and a first noise absorbance ratio of the first noise component is equal to or larger than a first predetermined value;
  a second determining section that, when it is determined that the first difference is smaller than the first predetermined value, determines whether a second difference between a second signal absorbance ratio of the second signal component and a second noise absorbance ratio of the second noise component is equal to or larger than a second predetermined value;
  a third determining section that, when it is determined that the second difference is smaller than the second predetermined value, determines whether a third difference between a third signal absorbance ratio of the third signal component and a third noise absorbance ratio of the third noise component is equal to or larger than a third predetermined value; and
  a concentration calculating section that,
    when it is determined that the first difference is equal to or larger than the first predetermined value, calculates a concentration of a light absorption material in blood of the subject based on a fundamental frequency of the first signal component,
    when it is determined that the first difference is smaller than the first predetermined value and the second difference is equal to or larger than the second predetermined value, calculates the concentration of the light absorption material in blood based on a fundamental frequency of the second signal component, or
    when it is determined that the first difference is smaller than the first predetermined value, the second difference is smaller than the second predetermined value, and the third difference is equal to or larger than the third predetermined value, calculates the concentration of the light absorption material in blood based on a fundamental frequency of the third signal component.

7. The pulse photometer according to claim 6, further comprising:
  a display that outputs an error state in response to the third determining section determining that the third difference is smaller than the third predetermined value.

8. A method of controlling a pulse photometer, the method comprising:
  emitting a first light beam of a first wavelength, a second light beam of a second wavelength, a third light beam of a third wavelength, and a fourth light beam of a fourth wavelength;
  outputting a first intensity signal in accordance with a first intensity of the first light beam that transmitted through or reflected from a living tissue of a subject, a second intensity signal in accordance with a second intensity of the second light beam that is transmitted through or reflected from the living tissue of the subject, a third intensity signal in accordance with a third intensity of the third light beam that is transmitted through or reflected from the living tissue of the subject, and a fourth intensity signal in accordance with a fourth intensity of the fourth light beam that is transmitted through or reflected from the living tissue of the subject, separating a first signal component of a first observed signal pair made of two of the first to fourth intensity signals from a first noise component of the first observed signal pair;

separating a second signal component of a second observed signal pair made of two of the first to fourth intensity signals excluding a combination of the first to fourth intensity signals in the first observed signal pair from a second noise component of the second observed signal pair;

separating a third signal component of a third observed signal pair made of two of the first to fourth intensity signals excluding combinations of the first to fourth intensity signals in the first and second observed signal pairs from a third noise component of the third observed signal pair;

determining whether a first difference between a first signal absorbance ratio of the first signal component and a first noise absorbance ratio of the first noise component is equal to or larger than a first predetermined value;

determining whether a second difference between a second signal absorbance ratio of the second signal component and a second noise absorbance ratio of the second noise component is equal to or larger than a second predetermined value;

when it is determined that the first difference is smaller than the first predetermined value and the second difference is smaller than the second predetermined value, determining whether a third difference between a third signal absorbance ratio of the third signal component and a third noise absorbance ratio of the third noise component is equal to or larger than a third predetermined value; and calculating a concentration of a light absorption material in blood of the subject based on a fundamental frequency of the first signal component, the concentration of the light absorption material in blood based on a fundamental frequency of the second signal component, or the concentration of the light absorption material in blood based on a fundamental frequency of the third signal component in response to determining that the first difference is smaller than the first predetermined value and determining that the second difference is smaller than the second predetermined value.

9. The method according to claim 8, wherein the third light beam is an infrared red light beam, and
wherein the first light beam and the second light beam are red light beams of different wavelengths.

10. The method according to claim 8, further comprising:
outputting an error state in response to determining that the first difference is smaller than the first predetermined value, determining that the second difference is smaller than the second predetermined value, and determining that the third difference is smaller than the third predetermined value.

11. The method according to claim 8, wherein the first wavelength, the second wavelength, and the third wavelength are selected from 660 nm, 700 nm, 730 nm, and 880 nm.

12. The method according to claim 8, wherein the first wavelength, the second wavelength, and the third wavelength are selected from are 660 nm, 700 nm, 880 nm, and 940 nm.

13. A method of controlling a pulse photometer, the method comprising:
emitting a first light beam of a first wavelength, a second light beam of a second wavelength, a third light beam of a third wavelength, and a fourth light beam of a fourth wavelength;

outputting a first intensity signal in accordance with a first intensity of the first light beam that transmitted through or reflected from a living tissue of a subject, a second intensity signal in accordance with a second intensity of the second light beam that is transmitted through or reflected from the living tissue of the subject, a third intensity signal in accordance with a third intensity of the third light beam that is transmitted through or reflected from the living tissue of the subject, and a fourth intensity signal in accordance with a fourth intensity of the fourth light beam that is transmitted through or reflected from the living tissue of the subject;

separating a first signal component of a first observed signal pair made of two of the first to fourth intensity signals from a first noise component of the first observed signal pair;

separating a second signal component of a second observed signal pair made of two of the first to fourth intensity signals excluding a combination of the first to fourth intensity signals in the first observed signal pair from a second noise component of the second observed signal pair;

separating a third signal component of a third observed signal pair made of two of the first to fourth intensity signals excluding combinations of the first to fourth intensity signals in the first and second observed signal pairs from a third noise component of the third observed signal pair;

determining whether a first difference between a first signal absorbance ratio of the first signal component and a first noise absorbance ratio of the first noise component is equal to or larger than a first predetermined value;

when it is determined that the first difference is smaller than the first predetermined value, determining whether a second difference between a second signal absorbance ratio of the second signal component and a second noise absorbance ratio of the second noise component is equal to or larger than a second predetermined value;

when it is determined that the second difference is smaller than the second predetermined value, determining whether a third difference between a third signal absorbance ratio of the third signal component and a third noise absorbance ratio of the third noise component is equal to or larger than a third predetermined value; and calculating:
when it is determined that the first difference is equal to or larger than the first predetermined value, a concentration of a light absorption material in blood of the subject based on a fundamental frequency of the first signal component, when it is determined that the first difference is smaller than the first predetermined value and the second difference is equal to or larger than the second predetermined value, the concentration of the light absorption material in blood based on a fundamental frequency of the second signal component, or when it is determined that the first difference is smaller than the first predetermined value, the second difference is smaller than the second predetermined value, and the third difference is equal to or larger than the third predetermined value, the concentration of the light absorption material in blood based on a fundamental frequency of the third signal component.

14. The method according to claim 13, further comprising:

outputting an error state in response to determining that the third difference is smaller than the third predetermined value.

* * * * *